(12) United States Patent
Bechtel et al.

(10) Patent No.: US 12,148,512 B2
(45) Date of Patent: Nov. 19, 2024

(54) PATIENT SAFETY USING VIRTUAL OBSERVATION

(71) Applicant: CERNER INNOVATION, INC., Kansas City, KS (US)

(72) Inventors: Todd Bechtel, Overland Park, KS (US); Lisa Schaberg, Lee's Summit, MO (US); Julie Hull, Kansas City, MO (US); Michelle Padgett, Leawood, KS (US)

(73) Assignee: Cerner Innovation, Inc., Kansas City, MO (US)

( * ) Notice: Subject to any disclaimer, the term of this patent is extended or adjusted under 35 U.S.C. 154(b) by 76 days.

(21) Appl. No.: 16/731,274

(22) Filed: Dec. 31, 2019

(65) Prior Publication Data

US 2021/0202052 A1    Jul. 1, 2021

(51) Int. Cl.
*G16H 10/60*        (2018.01)
*G16H 40/60*        (2018.01)
*G16H 50/30*        (2018.01)

(52) U.S. Cl.
CPC ............ *G16H 10/60* (2018.01); *G16H 40/60* (2018.01); *G16H 50/30* (2018.01)

(58) Field of Classification Search
CPC .......... G06F 16/00; G06F 30/10; G06F 30/20; G16H 10/60; G16H 50/30; G16H 40/60
See application file for complete search history.

(56) References Cited

U.S. PATENT DOCUMENTS

| | | |
|---|---|---|
| 1,860,487 A | 5/1932 | Thauss et al. |
| 4,669,263 A | 6/1987 | Sugiyama |
| 4,857,716 A | 8/1989 | Gombrich et al. |
| 5,031,228 A | 7/1991 | Lu |
| 5,276,432 A | 1/1994 | Travis |
| 5,448,221 A | 9/1995 | Weller |
| 5,482,050 A | 1/1996 | Smokoff et al. |

(Continued)

FOREIGN PATENT DOCUMENTS

| | | |
|---|---|---|
| DE | 19844918 A1 | 4/2000 |
| WO | 2007/081629 A2 | 7/2007 |

(Continued)

OTHER PUBLICATIONS

Non-Final Office action received for U.S. Appl. No. 16/410,745, mailed on May 21, 2021, 21 pages.

(Continued)

*Primary Examiner* — Rajesh Khattar
*Assistant Examiner* — Steven G. S. Sanghera
(74) *Attorney, Agent, or Firm* — Invoke

(57) ABSTRACT

Methods, systems, and computer-readable media are provided for improving patient safety using virtual observation. A falls risk assessment and a patient safety risk assessment are initially provided within an electronic health record of a patient. A clinician is prompted at a clinician device to provide input to the falls risk assessment and the patient safety risk assessment for the patient. Based on the input, a safety assessment score is determined for the patient. The safety assessment score is provided to the clinician via the clinician device and the clinician is prompted to initiate an order to place a camera in the room of the patient. Based on the order, a virtual sitter may be assigned to the patient to monitor the camera.

36 Claims, 10 Drawing Sheets

(56) References Cited

U.S. PATENT DOCUMENTS

| | | |
|---|---|---|
| 5,592,153 A | 1/1997 | Welling et al. |
| 5,798,798 A | 8/1998 | Rector et al. |
| 5,838,223 A | 11/1998 | Gallant et al. |
| 5,915,379 A | 6/1999 | Wallace et al. |
| 5,942,986 A | 8/1999 | Shabot et al. |
| 6,050,940 A | 4/2000 | Braun et al. |
| 6,095,984 A | 8/2000 | Amano et al. |
| 6,160,478 A | 12/2000 | Jacobsen et al. |
| 6,174,283 B1 | 1/2001 | Nevo et al. |
| 6,188,407 B1 | 2/2001 | Smith et al. |
| 6,269,812 B1 | 8/2001 | Wallace et al. |
| 6,287,452 B1 | 9/2001 | Allen et al. |
| 6,322,502 B1 | 11/2001 | Schoenberg et al. |
| 6,369,838 B1 | 4/2002 | Wallace et al. |
| 6,429,869 B1 | 8/2002 | Kamakura et al. |
| 6,614,349 B1 | 9/2003 | Proctor et al. |
| 6,727,818 B1 | 4/2004 | Wildman et al. |
| 6,804,656 B1 | 10/2004 | Rosenfeld et al. |
| 7,015,816 B2 | 3/2006 | Wildman et al. |
| 7,122,005 B2 | 10/2006 | Shusterman |
| 7,154,397 B2 | 12/2006 | Zerhusen et al. |
| 7,237,287 B2 | 7/2007 | Weismiller et al. |
| 7,323,991 B1 | 1/2008 | Eckert et al. |
| 7,408,470 B2 | 8/2008 | Wildman et al. |
| 7,420,472 B2 | 9/2008 | Tran |
| 7,430,608 B2 | 9/2008 | Noonan et al. |
| 7,502,498 B2 | 3/2009 | Wen et al. |
| 7,612,679 B1 | 11/2009 | Fackler et al. |
| 7,669,263 B2 | 3/2010 | Menkedick et al. |
| 7,715,387 B2 | 5/2010 | Schuman |
| 7,724,147 B2 | 5/2010 | Brown |
| 7,756,723 B2 | 7/2010 | Rosow et al. |
| 7,890,349 B2 | 2/2011 | Cole et al. |
| 7,893,842 B2 | 2/2011 | Deutsch |
| 7,895,055 B2 | 2/2011 | Schneider et al. |
| 7,908,153 B2 | 3/2011 | Scherpbier et al. |
| 7,945,457 B2 | 5/2011 | Zaleski |
| 7,962,544 B2 | 6/2011 | Torok et al. |
| 7,972,140 B2 | 7/2011 | Renaud |
| 8,090,155 B2 | 1/2012 | Lacey et al. |
| 8,108,036 B2 | 1/2012 | Tran |
| 8,123,685 B2 | 2/2012 | Brauers et al. |
| 8,128,596 B2 | 3/2012 | Carter |
| 8,190,447 B2 | 5/2012 | Hungerford et al. |
| 8,224,108 B2 | 7/2012 | Steinberg et al. |
| 8,237,558 B2 | 8/2012 | Seyed Momen et al. |
| 8,273,018 B1 | 9/2012 | Fackler et al. |
| 8,432,263 B2 | 4/2013 | Kunz |
| 8,451,314 B1 | 5/2013 | Cline et al. |
| 8,529,448 B2 | 9/2013 | McNair |
| 8,565,500 B2 | 10/2013 | Neff |
| 8,620,682 B2 | 12/2013 | Bechtel et al. |
| 8,655,680 B2 | 2/2014 | Bechtel et al. |
| 8,700,423 B2 | 4/2014 | Eaton, Jr. et al. |
| 8,727,961 B2 | 5/2014 | Ziv |
| 8,727,981 B2 | 5/2014 | Bechtel et al. |
| 8,769,153 B2 | 7/2014 | Dziubinski |
| 8,890,937 B2 | 11/2014 | Skubic et al. |
| 8,902,068 B2 | 12/2014 | Bechtel et al. |
| 8,917,186 B1 | 12/2014 | Grant |
| 8,953,886 B2 | 2/2015 | King et al. |
| 9,072,929 B1 | 7/2015 | Rush et al. |
| 9,129,506 B1 | 9/2015 | Kusens |
| 9,147,334 B2 | 9/2015 | Long et al. |
| 9,159,215 B1 | 10/2015 | Kusens |
| 9,269,012 B2 | 2/2016 | Fotland |
| 9,292,089 B1 | 3/2016 | Sadek |
| 9,305,191 B2 | 4/2016 | Long et al. |
| 9,330,987 B2 | 5/2016 | Lin et al. |
| 9,367,270 B1 | 6/2016 | Robertson |
| 9,368,014 B1* | 6/2016 | Bittman ................ G08B 25/08 |
| 9,408,561 B2 | 8/2016 | Stone et al. |
| 9,424,699 B2 | 8/2016 | Kusens et al. |
| 9,466,163 B2 | 10/2016 | Kusens et al. |
| 9,489,820 B1 | 11/2016 | Kusens |
| 9,519,215 B2 | 12/2016 | Robinson et al. |
| 9,519,969 B1 | 12/2016 | Kusens |
| 9,524,443 B1 | 12/2016 | Kusens |
| 9,536,310 B1 | 1/2017 | Kusens |
| 9,538,158 B1 | 1/2017 | Rush et al. |
| 9,563,955 B1 | 2/2017 | Kamarshi et al. |
| 9,597,016 B2 | 3/2017 | Stone et al. |
| 9,691,206 B2 | 6/2017 | Kusens et al. |
| 9,729,833 B1 | 8/2017 | Kusens |
| 9,741,227 B1 | 8/2017 | Kusens |
| 9,774,991 B2 | 9/2017 | Kusens |
| 9,838,849 B2 | 12/2017 | Kusens |
| 9,858,741 B2 | 1/2018 | Kusens et al. |
| 9,892,310 B2 | 2/2018 | Kusens et al. |
| 9,892,311 B2 | 2/2018 | Kusens et al. |
| 9,892,611 B1 | 2/2018 | Kusens |
| 9,905,113 B2 | 2/2018 | Kusens |
| 9,934,427 B2* | 4/2018 | Derenne ................ A61B 5/002 |
| 9,984,521 B1 | 5/2018 | Kusens et al. |
| 9,997,001 B2 | 6/2018 | Kusens et al. |
| 9,998,857 B2 | 6/2018 | Kusens |
| 10,013,831 B1 | 7/2018 | Kusens et al. |
| 10,055,961 B1 | 8/2018 | Johnson et al. |
| 10,078,956 B1 | 9/2018 | Kusens |
| 10,090,068 B2 | 10/2018 | Kusens et al. |
| 10,091,463 B1 | 10/2018 | Kusens |
| 10,096,223 B1 | 10/2018 | Kusens |
| 10,109,179 B2 | 10/2018 | Kusens |
| 10,115,253 B2 | 10/2018 | Kusens et al. |
| 10,115,254 B1 | 10/2018 | Kusens et al. |
| 10,121,299 B2 | 11/2018 | Kusens et al. |
| 10,127,788 B2* | 11/2018 | Wiggermann ....... A61B 5/1071 |
| 10,210,378 B2 | 2/2019 | Kusens et al. |
| 10,225,522 B1 | 3/2019 | Kusens |
| 10,276,019 B2 | 4/2019 | Johnson et al. |
| 10,342,478 B2 | 7/2019 | Kusens |
| 10,524,722 B2 | 1/2020 | Kusens et al. |
| 10,643,061 B2 | 5/2020 | Kusens et al. |
| 10,643,446 B2 | 5/2020 | Kusens et al. |
| 10,878,220 B2 | 12/2020 | Kusens |
| 10,922,936 B2 | 2/2021 | Kusens et al. |
| 10,922,946 B2 | 2/2021 | Kusens et al. |
| 2002/0015034 A1 | 2/2002 | Malmborg |
| 2002/0038073 A1 | 3/2002 | August |
| 2002/0077863 A1 | 6/2002 | Rutledge et al. |
| 2002/0101349 A1 | 8/2002 | Rojas, Jr. |
| 2002/0115905 A1 | 8/2002 | August |
| 2002/0183976 A1 | 12/2002 | Pearce |
| 2003/0037786 A1 | 2/2003 | Biondi et al. |
| 2003/0070177 A1 | 4/2003 | Kondo et al. |
| 2003/0092974 A1 | 5/2003 | Santoso et al. |
| 2003/0095147 A1 | 5/2003 | Daw |
| 2003/0135390 A1 | 7/2003 | O'Brien et al. |
| 2003/0140928 A1 | 7/2003 | Bui et al. |
| 2003/0227386 A1 | 12/2003 | Pulkkinen et al. |
| 2004/0019900 A1 | 1/2004 | Knightbridge et al. |
| 2004/0052418 A1 | 3/2004 | DeLean |
| 2004/0054760 A1 | 3/2004 | Ewing et al. |
| 2004/0097227 A1 | 5/2004 | Siegel |
| 2004/0116804 A1 | 6/2004 | Mostafavi |
| 2004/0193449 A1 | 9/2004 | Wildman et al. |
| 2005/0038326 A1 | 2/2005 | Mathur |
| 2005/0182305 A1 | 8/2005 | Hendrich |
| 2005/0231341 A1 | 10/2005 | Shimizu |
| 2005/0249139 A1 | 11/2005 | Nesbit |
| 2006/0004606 A1 | 1/2006 | Wendl et al. |
| 2006/0047538 A1 | 3/2006 | Condurso et al. |
| 2006/0049936 A1 | 3/2006 | Collins et al. |
| 2006/0058587 A1 | 3/2006 | Heimbrock et al. |
| 2006/0089541 A1 | 4/2006 | Braun et al. |
| 2006/0092043 A1 | 5/2006 | Lagassey |
| 2006/0107295 A1 | 5/2006 | Margis et al. |
| 2006/0145874 A1 | 7/2006 | Fredriksson et al. |
| 2006/0261974 A1 | 11/2006 | Albert et al. |
| 2007/0033072 A1* | 2/2007 | Bildirici ................ G09B 19/00 705/3 |
| 2007/0083445 A1 | 4/2007 | Garcia et al. |
| 2007/0085690 A1 | 4/2007 | Tran |
| 2007/0118054 A1 | 5/2007 | Pinhas et al. |

(56) References Cited

U.S. PATENT DOCUMENTS

| | | |
|---|---|---|
| 2007/0120689 A1 | 5/2007 | Zerhusen et al. |
| 2007/0129983 A1 | 6/2007 | Scherpbier et al. |
| 2007/0136102 A1 | 6/2007 | Rodgers |
| 2007/0136218 A1 | 6/2007 | Bauer et al. |
| 2007/0159332 A1 | 7/2007 | Koblasz |
| 2007/0279219 A1 | 12/2007 | Warriner |
| 2007/0296600 A1 | 12/2007 | Dixon et al. |
| 2008/0001735 A1 | 1/2008 | Tran |
| 2008/0001763 A1 | 1/2008 | Raja et al. |
| 2008/0002860 A1 | 1/2008 | Super et al. |
| 2008/0004904 A1 | 1/2008 | Tran |
| 2008/0009686 A1 | 1/2008 | Hendrich |
| 2008/0015903 A1 | 1/2008 | Rodgers |
| 2008/0021731 A1 | 1/2008 | Rodgers |
| 2008/0071210 A1 | 3/2008 | Moubayed et al. |
| 2008/0087719 A1 | 4/2008 | Sahud |
| 2008/0106374 A1 | 5/2008 | Sharbaugh |
| 2008/0126132 A1 | 5/2008 | Warner et al. |
| 2008/0228045 A1 | 9/2008 | Gao et al. |
| 2008/0236132 A1 | 10/2008 | Molnar |
| 2008/0249376 A1 | 10/2008 | Zaleski |
| 2008/0267447 A1 | 10/2008 | Kelusky et al. |
| 2008/0277486 A1 | 11/2008 | Seem et al. |
| 2008/0281638 A1 | 11/2008 | Weatherly et al. |
| 2009/0082829 A1 | 3/2009 | Panken et al. |
| 2009/0091458 A1 | 4/2009 | Deutsch |
| 2009/0099480 A1 | 4/2009 | Salgo et al. |
| 2009/0112630 A1 | 4/2009 | Collins et al. |
| 2009/0119843 A1 | 5/2009 | Rodgers et al. |
| 2009/0177327 A1 | 7/2009 | Turner et al. |
| 2009/0224924 A1 | 9/2009 | Thorp |
| 2009/0278934 A1 | 11/2009 | Ecker et al. |
| 2009/0322513 A1 | 12/2009 | Hwang et al. |
| 2009/0326340 A1 | 12/2009 | Wang et al. |
| 2010/0117836 A1 | 5/2010 | Seyed Momen et al. |
| 2010/0169114 A1 | 7/2010 | Henderson et al. |
| 2010/0169120 A1 | 7/2010 | Herbst et al. |
| 2010/0172567 A1 | 7/2010 | Prokoski |
| 2010/0176952 A1 | 7/2010 | Bajcsy et al. |
| 2010/0188228 A1 | 7/2010 | Hyland |
| 2010/0205771 A1 | 8/2010 | Pietryga et al. |
| 2010/0245577 A1 | 9/2010 | Yamamoto et al. |
| 2010/0285771 A1 | 11/2010 | Peabody |
| 2010/0305466 A1 | 12/2010 | Corn |
| 2011/0018709 A1 | 1/2011 | Kornbluh |
| 2011/0022981 A1 | 1/2011 | Mahajan et al. |
| 2011/0025493 A1 | 2/2011 | Papadopoulos et al. |
| 2011/0025499 A1 | 2/2011 | Hoy et al. |
| 2011/0035057 A1 | 2/2011 | Receveur et al. |
| 2011/0035466 A1 | 2/2011 | Panigrahi |
| 2011/0054936 A1 | 3/2011 | Cowan et al. |
| 2011/0068930 A1 | 3/2011 | Wildman et al. |
| 2011/0077965 A1 | 3/2011 | Nolte et al. |
| 2011/0087079 A1 | 4/2011 | Aarts |
| 2011/0087125 A1 | 4/2011 | Causevic |
| 2011/0087707 A1 | 4/2011 | Abraham |
| 2011/0102133 A1 | 5/2011 | Shaffer |
| 2011/0102181 A1 | 5/2011 | Metz et al. |
| 2011/0106560 A1 | 5/2011 | Eaton et al. |
| 2011/0106561 A1 | 5/2011 | Eaton et al. |
| 2011/0175809 A1 | 7/2011 | Markovic et al. |
| 2011/0190593 A1 | 8/2011 | McNair |
| 2011/0227740 A1 | 9/2011 | Wohltjen |
| 2011/0245707 A1 | 10/2011 | Castle et al. |
| 2011/0254682 A1 | 10/2011 | Sigrist Christensen |
| 2011/0288811 A1 | 11/2011 | Greene |
| 2011/0295621 A1 | 12/2011 | Farooq et al. |
| 2011/0301440 A1 | 12/2011 | Riley et al. |
| 2011/0313325 A1 | 12/2011 | Cuddihy |
| 2012/0016295 A1 | 1/2012 | Tsoukalis |
| 2012/0025991 A1 | 2/2012 | O'Keefe et al. |
| 2012/0026308 A1 | 2/2012 | Johnson et al. |
| 2012/0075464 A1 | 3/2012 | Derenne et al. |
| 2012/0092162 A1 | 4/2012 | Rosenberg |
| 2012/0098918 A1 | 4/2012 | Murphy |
| 2012/0140068 A1 | 6/2012 | Monroe et al. |
| 2012/0154582 A1 | 6/2012 | Johnson et al. |
| 2012/0212582 A1 | 8/2012 | Deutsch |
| 2012/0259650 A1 | 10/2012 | Mallon et al. |
| 2012/0314901 A1 | 12/2012 | Hanson et al. |
| 2012/0323090 A1 | 12/2012 | Bechtel et al. |
| 2012/0323591 A1 | 12/2012 | Bechtel et al. |
| 2012/0323592 A1 | 12/2012 | Bechtel et al. |
| 2013/0027199 A1 | 1/2013 | Bonner |
| 2013/0028570 A1 | 1/2013 | Suematsu et al. |
| 2013/0120120 A1 | 5/2013 | Long et al. |
| 2013/0122807 A1 | 5/2013 | Tenarvitz et al. |
| 2013/0127620 A1 | 5/2013 | Siebers et al. |
| 2013/0184592 A1 | 7/2013 | Venetianer et al. |
| 2013/0265482 A1 | 10/2013 | Funamoto |
| 2013/0309128 A1 | 11/2013 | Voegeli et al. |
| 2013/0332184 A1 | 12/2013 | Burnham et al. |
| 2014/0039351 A1 | 2/2014 | Mix et al. |
| 2014/0070950 A1 | 3/2014 | Snodgrass |
| 2014/0081654 A1 | 3/2014 | Bechtel et al. |
| 2014/0085501 A1 | 3/2014 | Tran |
| 2014/0086450 A1 | 3/2014 | Huang et al. |
| 2014/0108041 A1 | 4/2014 | Bechtel et al. |
| 2014/0155755 A1 | 6/2014 | Pinter et al. |
| 2014/0168397 A1* | 6/2014 | Greco .................... G16H 30/20 348/77 |
| 2014/0191861 A1 | 7/2014 | Scherrer |
| 2014/0191946 A1 | 7/2014 | Cho et al. |
| 2014/0213845 A1 | 7/2014 | Bechtel et al. |
| 2014/0267625 A1 | 9/2014 | Clark et al. |
| 2014/0267736 A1 | 9/2014 | Delean |
| 2014/0309789 A1 | 10/2014 | Ricci |
| 2014/0327545 A1 | 11/2014 | Bolling et al. |
| 2014/0328512 A1 | 11/2014 | Gurwicz et al. |
| 2014/0333744 A1 | 11/2014 | Baym et al. |
| 2014/0333776 A1 | 11/2014 | Dedeoglu et al. |
| 2014/0354436 A1 | 12/2014 | Nix et al. |
| 2014/0365242 A1 | 12/2014 | Neff |
| 2015/0057635 A1 | 2/2015 | Bechtel et al. |
| 2015/0061891 A1 | 3/2015 | Oleson et al. |
| 2015/0109442 A1 | 4/2015 | Derenne et al. |
| 2015/0148943 A1* | 5/2015 | Sullivan ................ A61J 7/0076 700/231 |
| 2015/0206415 A1 | 7/2015 | Wegelin et al. |
| 2015/0221202 A1* | 8/2015 | Russell ................ A61B 5/1117 340/573.7 |
| 2015/0238722 A1* | 8/2015 | Al-Ali ................ A61M 16/085 128/205.13 |
| 2015/0269318 A1 | 9/2015 | Neff |
| 2015/0278456 A1 | 10/2015 | Bermudez Rodriguez et al. |
| 2015/0294143 A1 | 10/2015 | Wells et al. |
| 2016/0022218 A1 | 1/2016 | Hayes et al. |
| 2016/0070869 A1 | 3/2016 | Portnoy |
| 2016/0093195 A1 | 3/2016 | Ophardt |
| 2016/0098676 A1 | 4/2016 | Kusens et al. |
| 2016/0127641 A1 | 5/2016 | Gove |
| 2016/0180668 A1 | 6/2016 | Kusens et al. |
| 2016/0183864 A1 | 6/2016 | Kusens et al. |
| 2016/0217347 A1 | 7/2016 | Mineo |
| 2016/0253802 A1 | 9/2016 | Venetianer et al. |
| 2016/0267327 A1 | 9/2016 | Franz et al. |
| 2016/0285416 A1 | 9/2016 | Tiwari et al. |
| 2016/0314258 A1 | 10/2016 | Kusens |
| 2016/0324460 A1 | 11/2016 | Kusens |
| 2016/0360970 A1 | 12/2016 | Tzvieli et al. |
| 2017/0055917 A1 | 3/2017 | Stone et al. |
| 2017/0084158 A1 | 3/2017 | Kusens |
| 2017/0091562 A1 | 3/2017 | Kusens |
| 2017/0109991 A1 | 4/2017 | Kusens |
| 2017/0116473 A1 | 4/2017 | Sashida et al. |
| 2017/0143240 A1 | 5/2017 | Stone et al. |
| 2017/0147770 A1* | 5/2017 | Xu ....................... A61B 5/7275 |
| 2017/0163949 A1 | 6/2017 | Suzuki |
| 2017/0193177 A1 | 7/2017 | Kusens |
| 2017/0193279 A1 | 7/2017 | Kusens et al. |
| 2017/0193772 A1 | 7/2017 | Kusens et al. |
| 2017/0195637 A1 | 7/2017 | Kusens et al. |
| 2017/0214902 A1 | 7/2017 | Braune |
| 2017/0289503 A1 | 10/2017 | Kusens |

(56) References Cited

U.S. PATENT DOCUMENTS

| | | | |
|---|---|---|---|
| 2017/0337682 A1 | 11/2017 | Liao et al. | |
| 2018/0018864 A1 | 1/2018 | Baker | |
| 2018/0068545 A1 | 3/2018 | Kusens | |
| 2018/0104409 A1 | 4/2018 | Bechtel et al. | |
| 2018/0114053 A1 | 4/2018 | Kusens et al. | |
| 2018/0116528 A1 | 5/2018 | Tzvieli et al. | |
| 2018/0137340 A1 | 5/2018 | Kusens et al. | |
| 2018/0144605 A1 | 5/2018 | Kusens | |
| 2018/0189946 A1 | 7/2018 | Kusens et al. | |
| 2018/0190098 A1 | 7/2018 | Kusens | |
| 2018/0357875 A1 | 12/2018 | Kusens | |
| 2019/0006046 A1 | 1/2019 | Kusens et al. | |
| 2019/0029528 A1 | 1/2019 | Tzvieli et al. | |
| 2019/0043192 A1 | 2/2019 | Kusens et al. | |
| 2019/0057592 A1 | 2/2019 | Kusens | |
| 2019/0122028 A1 | 4/2019 | Kusens et al. | |
| 2019/0205630 A1 | 7/2019 | Kusens | |
| 2019/0206218 A1 | 7/2019 | Kusens et al. | |
| 2019/0209022 A1* | 7/2019 | Sobol | A61B 5/7435 |
| 2019/0228866 A1 | 7/2019 | Weffers-Albu et al. | |
| 2019/0253668 A1 | 8/2019 | Kusens | |
| 2019/0261915 A1 | 8/2019 | Kusens | |
| 2019/0307405 A1* | 10/2019 | Terry | A61F 13/42 |
| 2019/0318149 A1 | 10/2019 | Kusens et al. | |
| 2019/0318478 A1 | 10/2019 | Kusens et al. | |
| 2020/0050844 A1 | 2/2020 | Kusens | |
| 2020/0143643 A1 | 5/2020 | Kusens et al. | |
| 2020/0226905 A1 | 7/2020 | Kusens et al. | |
| 2021/0298686 A1* | 9/2021 | Zhao | G16H 10/60 |

FOREIGN PATENT DOCUMENTS

| | | | |
|---|---|---|---|
| WO | 2009/018422 A1 | 2/2009 | |
| WO | 2012/122002 A1 | 9/2012 | |
| WO | 2016/126845 A1 | 8/2016 | |
| WO | 2017/058991 A1 | 4/2017 | |
| WO | 2017/124056 A1 | 7/2017 | |
| WO | 2018/218286 A1 | 12/2018 | |

OTHER PUBLICATIONS

"Camera System is Part of an Automated Hand Hygiene Monitoring System", Infection Control Today, Jul. 15, 2011, pp. 1-6.
Conaire et al., "Fusion Of Infrared and Visible Spectrum Video for Indoor Surveillance", WIAMIS, Apr. 2005, 4 pages.
Final Office Action received for U.S. Appl. No. 13/731,235, mailed on Apr. 14, 2017, 15 pages.
Final Office Action received for U.S. Appl. No. 13/731,235, mailed on Apr. 18, 2018, 15 pages.
Final Office Action received for U.S. Appl. No. 14/084,588, mailed on Dec. 19, 2014, 24 pages.
Final Office Action received for U.S. Appl. No. 14/611,363, mailed on Apr. 28, 2017, 20 pages.
Final Office Action received for U.S. Appl. No. 14/623,349, mailed on Oct. 4, 2017, 29 pages.
Final Office Action received for U.S. Appl. No. 14/724,969, mailed on Jul. 28, 2016, 26 pages.
Final Office Action received for U.S. Appl. No. 15/395,243, mailed on Jun. 11, 2019, 18 pages.
First Action Interview received for U.S. Appl. No. 14/088,923, mailed on Aug. 25, 2017, 6 pages.
First Action Interview received for U.S. Appl. No. 13/339,828, mailed on Oct. 28, 2013, 5 pages.
First Action Interview received for U.S. Appl. No. 13/731,235, mailed on Aug. 8, 2016, 6 pages.
First Action Interview received for U.S. Appl. No. 14/529,432, mailed on May 14, 2018, 6 pages.
Hong, Eliane, "[WoHIT] Hand Hygiene Being Taught in Hospitals via Social Gaming", L'Atelier BNP Paribas, Health, Apr. 2014, 6 pages.
Pre-interview First Office Action received for U.S. Appl. No. 14/529,432, mailed on Mar. 5, 2018, 4 pages.
Mooney, Tom, "Rhode Island ER First To Test Google Glass on Medical Conditions", EMS1, Available online at: <https://www.ems1.com/ems-products/technology/articles/1860487-Rhode-Island-ER-first-to-test-Google-Glass-on-medical-conditions/>, Mar. 10, 2014, 3 pages.
Non Final Office Action received for U.S. Appl. No. 15/395,243, mailed on Feb. 14, 2019, 14 pages.
Non Final Office Action received for U.S. Appl. No. 16/107,567, mailed on Mar. 29, 2019, 8 pages.
Non-Final Office Action received for U.S. Appl. No. 13/543,816, mailed on Dec. 1, 2014, 18 pages.
Non-Final Office Action received for U.S. Appl. No. 13/731,235, mailed on Aug. 1, 2018, 18 pages.
Non-Final Office Action received for U.S. Appl. No. 14/084,588, mailed on Jul. 16, 2014, 12 pages.
Non-Final Office Action received for U.S. Appl. No. 14/339,397, mailed on Oct. 7, 2015, 16 pages.
Non-Final Office Action received for U.S. Appl. No. 14/575,850, mailed on Mar. 11, 2016, 10 pages.
Non-Final Office Action received for U.S. Appl. No. 14/599,498, mailed on May 31, 2017, 24 pages.
Non-Final Office Action received for U.S. Appl. No. 14/611,363, mailed on Jan. 11, 2017, 19 pages.
Non-Final Office Action received for U.S. Appl. No. 14/623,349, mailed on Apr. 5, 2017, 15 pages.
Non-Final Office Action received for U.S. Appl. No. 14/724,969, mailed on Feb. 11, 2016, 14 pages.
Non-Final Office Action received for U.S. Appl. No. 14/727,434, mailed on Sep. 23, 2016, 9 pages.
Non-Final Office Action received for U.S. Appl. No. 14/757,593, mailed on Aug. 16, 2017, 8 pages.
Non-Final Office Action received for U.S. Appl. No. 14/757,877, mailed on Feb. 23, 2017, 24 pages.
Non-Final Office Action received for U.S. Appl. No. 15/134,189, mailed on May 9, 2019, 30 pages.
Non-Final Office Action received for U.S. Appl. No. 15/285,416, mailed on Apr. 11, 2017, 13 pages.
Non-Final Office Action received for U.S. Appl. No. 15/395,526, mailed on Apr. 27, 2017, 16 pages.
Non-Final Office Action received for U.S. Appl. No. 15/395,762, mailed on May 1, 2019, 27 pages.
Non-Final Office Action received for U.S. Appl. No. 15/395,762, mailed on May 31, 2018, 24 pages.
Non-Final Office Action received for U.S. Appl. No. 15/628,318, mailed on Jun. 8, 2018, 9 pages.
Non-Final Office Action received for U.S. Appl. No. 15/856,419, mailed on May 2, 2019, 8 pages.
Non-Final Office Action received for U.S. Appl. No. 13/543,816, mailed on Dec. 30, 2013, 9 pages.
Notice of Allowance received for U.S. Appl. No. 13/339,828, mailed on Jan. 3, 2014, 10 pages.
Notice of Allowance received for U.S. Appl. No. 14/141,636, mailed on Jul. 31, 2014, 8 pages.
Notice of Allowance received for U.S. Appl. No. 14/613,866, mailed on Mar. 20, 2017, 11 pages.
Notice of Allowance received for U.S. Appl. No. 15/857,696, mailed on Jul. 16, 2019, 9 pages.
Notice of Allowance received for U.S. Appl. No. 16/380,013, mailed on Jul. 10, 2019, 10 pages.
Pre-Interview First Office Action received for U.S. Appl. No. 13/164,167, mailed on Mar. 15, 2013, 4 pages.
Pre-Interview First Office Action received for U.S. Appl. No. 13/235,837, mailed on May 23, 2013, 4 pages.
Pre-Interview First Office Action received for U.S. Appl. No. 13/339,828, mailed on Sep. 10, 2013, 5 pages.
Pre-Interview First Office Action received for U.S. Appl. No. 13/731,235, mailed on Apr. 7, 2016, 4 pages.
Pre-interview First Office Action received for U.S. Appl. No. 14/088,923, mailed on Jun. 30, 2017, 4 pages.
Pre-interview First Office Action received for U.S. Appl. No. 14/244,160, mailed on Sep. 28, 2017, 4 pages.

(56) References Cited

OTHER PUBLICATIONS

Pre-Interview First Office action received for U.S. Appl. No. 16/816,626, mailed on Dec. 22, 2020, 4 pages.
Notice of Allowance received for U.S. Appl. No. 16/181,897, mailed on Oct. 14, 2020, 9 pages.
Preinterview First Office Action received for U.S. Appl. No. 16/832,790, mailed on Aug. 25, 2020, 5 pages.
Final Office Action received for U.S. Appl. No. 15/134,189, mailed on May 6, 2020, 31 pages.
Preinterview First Office Action received for U.S. Appl. No. 16/181,897 mailed on May 11, 2020, 5 pages.
Preinterview First Office action received for U.S. Appl. No. 15/857,696, mailed on May 23, 2019, 14 pages.
Pre-interview First Office Action received for U.S. Appl. No. 15/910,645, mailed on May 21, 2018, 14 pages.
Raheja et al., "Human Facial Expression Detection From Detected in Captured Image Using Back Propagation Neural Network", International Journal of Computer Science and Information Technology (IJCSIT), vol. 2, No. 1, Feb. 2010, 9 pages.
"Virtual Patient Observation: Centralize Monitoring of High-Risk Patients with Video", CISCO, Cisco Video Surveillance Manager, 2013, pp. 1-6.
Notice of Allowance received for U.S. Appl. No. 16/654,502, mailed on Feb. 17, 2021, 9 pages.
Non-Final Office action received for U.S. Appl. No. 17/117,414, mailed on Jul. 27, 2021, 12 pages.
Non-Final Office Action received for U.S. Appl. No. 16/830,498, mailed on Sep. 22, 2021, 29 pages.
Non-Final Office Action received for U.S. Appl. No. 17/101,639, mailed on Sep. 13, 2021, 2021, 13 pages.
Notice of Allowance received for U.S. Appl. No. 16/816,626, mailed on Sep. 30, 2021, 9 pages.
Quan et al., "Facial Asymmetry Analysis Based on 3-D Dynamic Scans", 2012 IEEE International Conference on Systems, Man, and Cybernetics; COEX, Seoul, Korea; DOI: 10.1109/ICSMC.2012.6378151, Oct. 14-17, 2012, pp. 2676-2681.
Non-Final Office Action received for U.S. Appl. No. 17/152,403, mailed on Mar. 15, 2022, 10 pages.
Non-Final Office Action received for U.S. Appl. No. 17/101,639, mailed on Aug. 2, 2022, 13 pages.
Notice of Allowance received for U.S. Appl. No. 17/318,521, mailed on Aug. 31, 2022, 9 pages.
Otanasap et al., "Pre-Impact Fall Detection System Using Dynamic Threshold and 3D Bounding Box", SPIE.Digital Library, Proceedings vol. 10225, Eighth International Conference on Graphic and Image Processing (ICGIP 2016), Available online at: <https://doi.org/10.1117/12.2266822>, Feb. 8, 2017, pp. 1-6.
Zarka et al., "Real-Time Human Motion Detection and Tracking", IEEE, Available online at: <https://ieeexplore.ieee.org/document/4530098>, 2008, pp. 1-6.
Notice of Allowance received for U.S. Appl. No. 16/410,745, mailed on Jan. 4, 2022, 10 pages.

\* cited by examiner

| Nursing -- Telemetry Admission PowerPlan (Initiated Pending) | | |
|---|---|---|
| ☐ | Adult Admission Assessment | |
| ☐ | Height Weight Admission Screening | |
| ☐ | Adult Database Eligibility | |
| ☐ | Patient Safety and Orientatoin | T;N |
| ☐ | Adult Ongoing Assessment | T;N+60, Telemetry Assmt |
| ☐ | Document in Care Plan | T;N, CarePlan |
| ☐ | Admission Skin/Fall Assessment | T;N |
| ☐ | Skin/Fall Assessment | QShift |
| ☐ | Device Daily Assessment | T;N, Q4AMAssmt |
| ☐ | *Vital Signs POC | PRN Indicator |
| ☐ | *Height Weight POC | PRN Indicator |
| ☐ | *ADL POC | PRN Indicator |
| ☐ | *Intake and Output POC | PRN Indicator |
| ☐ | Communication Board | T;N, QShift |
| ☐ | Discharge Needs IPOC -- Acute Care  Initiated Pen... | |
| ☐ | Nursing -- VTE Porphylaxis and Management IPOC  Initiated Pen... | |
| ☐ | Pain IPOC -- Acute Care  Initiated Pen... | |
| ☐ | Sodium Chloride 0.9% (Normal Saline 50mL IVPB Flush) | 25 mL, injection, As Needed, IVPush, PRN Flush 25mL per IVPB |
| ☐ | Patient Observer Safety Score | T;N, QShiftNow |
| ☐ | Fall Education Video | T;N, ONCE |
| +3 day | | |
| ☐ | Fall Education Video | T;N, ONCE |
| ☐ | Alarm Parameter Assessment | T;N, QShiftNow |

| Nurse Collect | Scheduled Patient Care | Continuous Patient Care | All PRN Tasks | Wound Care | PRN Patient Care |
|---|---|---|---|---|---|

Task retrieval completed

| Task Status | Scheduled Date and Time | Task Description | Order Details |
|---|---|---|---|
| Pending | 06/18/2019 14:00 CDT | Patient Observer Safety Observation | 06/18/2019 14:00:00 CDT Order placed based... |
| Pending | 06/18/2019 15:00 CDT | Patient Observer Safety Observation | 06/18/2019 15:00:00 CDT Order placed based... |
| Pending | 06/18/2019 16:00 CDT | Patient Observer Safety Observation | 06/18/2019 16:00:00 CDT |
| Pending | 06/18/2019 17:00 CDT | Patient Observer Safety Observation | |
| Pending | 06/18/2019 17:35 CDT | Safety Decision | |
| Pending | 06/18/2019 18:00 CDT | Patient Observer | |
| Pending | 06/18/2019 19:00 CDT | Patient Observer | |
| Pending | 06/18/2019 20:00 CDT | Patient Observer | |

702

06/18/19 14:00 CDT 13:37 CDT

Patient Activity
- ☐ Patient in bed, awake
- ☐ Patient in bed, appears with eyes closed
- ☐ Patient in chair, awake
- ☐ Patient in chair, appears with eyes closed
- ☐ Patient ambulating in room
- ☐ Patient in bathroom
- ☐ Provider at bedside
- ☐ Bedside care, privacy requested
- ☐ Visitors at bedside
- ☐ Observed fall

| Main Details | Secondary Buttons | | | |
|---|---|---|---|---|
| Remain Seated-Eng | Return To Bed-Eng | Remain Seated-SP | Return To Bed-SP | |
| Remain Seated-AR-F | Return To Bed-AR-F | Return To Bed-AR-M | Remain Seated-AR-M | |
| Remain To Bed-SO-F | Remain Seated-SO-F | Return To Bed-SO-M | Remain Seated-SO-M | |
| Edit Patient/Zones | Night Vision | Video On/Off | Import Camera | |
| Pixelate Face | Privacy | Audio On/Off | Remove Camera | |
| Reset Skeleton | Swap Skeletons | Reboot Room PC | Restart Camera | |
| Play Intro Video | | | | |

- Test Alert
- Bed Exit
- Room Exit
- Patient Assist
- Safety Warning
- Maintenance
- Patient Fell
- Med Request
- Food/Drink
- Staff Assist

800

PATIENT SAFETY USING VIRTUAL OBSERVATION

BACKGROUND

Medical facilities, such as hospitals, face many challenges in addition to simply caring for patients. In order to meet these challenges, fiscal responsibility is paramount. Continued surveillance and avoidance of "never events" like falls prevention remains a key factor in cost containment.

According to recent studies, falls are a leading cause of death among people over the age of 65 and 10% of the fatal falls for patients over 65 years of age occur in a hospital setting. Of these hospital-based falls, approximately 30% will result in a serious injury with the cost to care for these injuries estimated to reach $54.9 billion per year by 2020. Patients fall for a variety of reasons, including not calling for nursing assistance, the bed exit alarm not being set, patients being on high risk medications, and delays in communication when the nurse is called. Findings suggest that attention to optimizing patient care delivery results in a reduction in the occurrence of adverse events.

In some instances, patients require one-on-one monitoring to redirect risky behavior or address a patient's immediate needs that may otherwise result in falls. One-on-one monitoring allows for observing a change in a patient's condition quickly and accurately. However, such one-on-one monitoring is costly, decreases time caregivers can spend providing care, and results in dissatisfaction among staff.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present disclosure relate to systems and methods for providing improved safe patient care using virtual observation. More particularly, embodiments of the present disclosure utilize a virtual observation solution to enable trained observation technicians to monitor multiple patient rooms from a central monitoring station, reduce sitter labor costs, and prevent falls and other adverse events. To do so, a falls risk assessment and a patient safety risk assessment are initially provided within an electronic health record of a patient. A clinician is prompted at a clinician device to provide input to the falls risk assessment and the patient safety risk assessment for the patient. Based on the input, a safety assessment score is determined for the patient. The safety assessment score is provided to the clinician via the clinician device and the clinician is prompted to initiate an order to place a sitter at the bedside or place a camera in the room of the patient. Based on the order, a virtual sitter may be assigned to the patient to monitor the camera.

In some embodiments, the virtual sitter is prompted to provide documentation for the patient at a virtual observation interface. Upon receiving documentation from the virtual sitter device corresponding to patient behavior, the clinician determines whether to continue or discontinue the virtual sitter for the patient.

In some embodiments, virtual guardrails are assigned for the patient. The virtual guardrails may be three-dimensional (3D) zones positions around a patient bed or chair, safety zones to detect tampering with invasive line or tube placement, safety zones for staff safety, patient elopement zones that provide a wide angle of a patient room to detect elopement or visitor monitoring zones to prevent drug diversion and abuse.

BRIEF DESCRIPTION OF THE SEVERAL VIEWS OF THE DRAWING

The description references the attached drawing figures, wherein:

FIGS. 3-9 depict illustrative screen displays of virtual observation system, in accordance with embodiments of the present invention.

DETAILED DESCRIPTION

Figure 1:
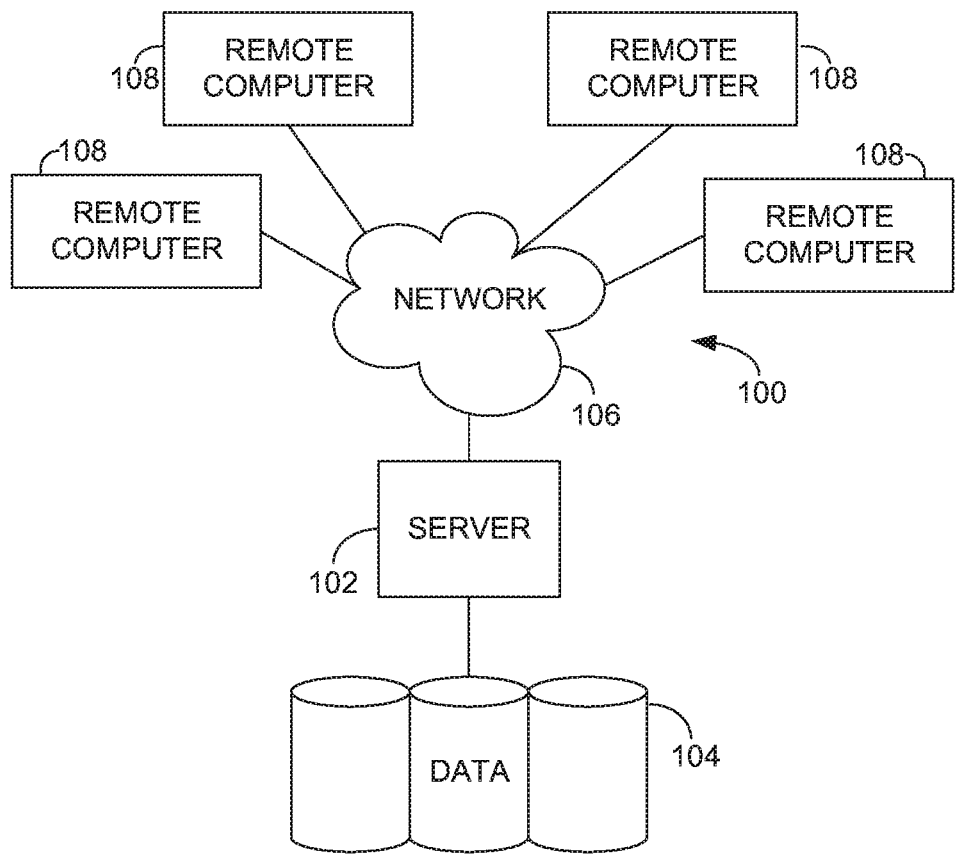
FIG. 1 is a block diagram of an exemplary operating environment suitable to implement embodiments of the present disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

As noted in the Background, medical facilities, such as hospitals, face many challenges in addition to simply caring for patients. In order to meet these challenges, fiscal responsibility is paramount. Continued surveillance and avoidance of "never events" like falls prevention remains a key factor in cost containment.

According to recent studies, falls are a leading cause of death among people over the age of 65 and 10% of the fatal falls for patients over 65 years of age occur in a hospital setting. Of these hospital-based falls, approximately 30% will result in a serious injury with the cost to care for these injuries estimated to reach $54.9 billion per year by 2020. Patients fall for a variety of reasons, including not calling for nursing assistance, the bed exit alarm not being set, patients being on high risk medications, and delays in communication when the nurse is called. "Findings suggest that attention to optimizing patient care delivery results in a reduction in the occurrence of adverse In some instances, patients require one-on-one monitoring to redirect risky behavior or address a patient's immediate needs that may otherwise result in falls. One-on-one monitoring allows for observing a change in a patient's condition quickly and accurately. However, such one-on-one monitoring is costly, decreases time caregivers can spend providing care, and results in dissatisfaction among staff.

Embodiments of the present disclosure relate to systems and methods for providing improved patient safety using virtual observation. More particularly, embodiments of the present disclosure utilize a virtual observation solution to enable trained observation technicians to monitor multiple patient rooms from a central monitoring station, reduce sitter labor costs, and prevent falls and other adverse events. To do so, a falls risk assessment and a patient safety risk assessment are initially provided within an electronic health record of a patient. A clinician is prompted at a clinician device to provide input to the falls risk assessment and the patient safety risk assessment for the patient. Based on the input, a safety assessment score is determined for the patient. The safety assessment score is provided to the clinician via the clinician device and the clinician is prompted to initiate an order to place a sitter at the bedside or place a camera in the room of the patient. Based on the order, a virtual sitter may be assigned to the patient to monitor the camera.

In some embodiments, the virtual sitter is prompted to provide documentation for the patient at a virtual observation interface. Upon receiving documentation from the virtual sitter device corresponding to patient behavior, the clinician determines whether to continue or discontinue the virtual sitter for the patient.

In some embodiments, virtual guardrails are assigned for the patient. The virtual guardrails may be 3D zones positions around a patient bed or chair, safety zones to detect tampering with invasive line or tube placement, safety zones for staff safety, patient elopement zones that provide a wide angle of a patient room to detect elopement, or visitor monitoring zones to prevent drug diversion and abuse.

Embodiments of the present invention maximize time caregivers can spend providing care at the bedside. This results in greater caregiver satisfaction and improves retention of staff. Moreover, occurrence of "never events" can be significantly reduced or avoided, altogether.

Embodiments of the present invention provide a virtual solution that uses 3D cameras to track patient movement and alert centralized monitoring staff if patients move beyond bed or room zones, need assistance, or interfere with lines or medical devices. The solution allows virtual monitoring technicians to communicate with patients and share patient assistance alerts with their assigned care team members via a mobile device (e.g., Zebra® TC51). Integration between the EHR and the mobile device facilitates care team assignments and ensures alerts and communications are routed to the appropriate care team members. The integration between the virtual sitter technology and the communication devices work in concert with each other. For example, when virtual sitters identify a patient at risk for falling, they can notify that patient's nurse and/or the appropriate care team easily and quickly with the touch of a single button. All documentation generated or utilized by the virtual observation system is integrated with the EHR of the patient.

In embodiments, the virtual observation system enables one virtual sitter to observe up to twelve patients, allows more primary care technicians to be available on the floor to assist nurses with day-to-day activities, which in turn allows nurses and/or the appropriate care team to spend more with patients. The virtual observation system drives the algorithms and the communications to the care team based on patient care assignments. A central monitoring station is staffed with virtual sitters, and assignment-based alerts and communications are pushed to the correct care team members. An end-user device team is available to assist with camera management.

In some embodiments, machine learning algorithms are employed to learn which patients are identified and selected for virtual observation. Data and information may be captured over time and the machine learning algorithms can be trained to predict or suggest when a patient is similar to another patient that has been previously assigned a virtual sitter. Additionally or alternatively, the machine learning algorithms can be trained to determine when a falls risk assessment and a patient safety risk assessment should be provided within an electronic health record of a patient, when a virtual sitter should prompted to provide documentation for the patient at a virtual observation interface, or when the clinician should be prompted to determine whether to continue or discontinue the virtual sitter for the patient. The machine learning algorithms may also be trained to predict where the virtual guardrails should be positioned by the virtual sitter (i.e., based on similarities to other patients).

Although described with respect to falls risk and patient safety risk, embodiments of the present invention may additionally benefit patients under seizure watch or behavioral health and general safety concerns within a controlled environment. In each of these settings, embodiments of the present invention could reduce the required physical presence and improve the patient experience.

Accordingly, one embodiment of the present disclosure is directed to a system. The system includes a processor; and a computer storage medium storing computer-usable instructions that, when used by the processor, cause the processor to: provide a falls risk assessment and a patient safety risk assessment within an electronic health record of a patient; prompt a clinician at a clinician device to provide input to the falls risk assessment and the patient safety risk assessment for the patient; based on the input, determine a safety assessment score for the patient; provide the safety assessment score of the patient to the clinician via the clinician device prompt the clinician to initiate an order to place a camera in the room of the patient; and based on the order, assign a virtual sitter to the patient.

In another embodiment, the present disclosure directed to a computerized method. The method includes providing a falls risk assessment and a patient safety risk assessment within an electronic health record of a patient. The method also includes prompting a clinician at a clinician device to provide input to the falls risk assessment and the patient safety risk assessment for the patient. The method further includes, based on the input, determining a safety assessment score for the patient. The method also includes providing the safety assessment score of the patient to the clinician via the clinician device. The method further includes prompting the clinician to initiate an order to place a camera in the room of the patient. The method also includes, based on the order, assigning a virtual sitter to the patient. The method further includes prompting the virtual sitter to provide documentation for the patient at a virtual observation interface. The method also includes, upon receiving documentation from the virtual sitter device corresponding to patient behavior, prompting the clinician to determine whether to continue or discontinue the virtual sitter for the patient.

In yet another embodiment, the present disclosure is directed to one or more computer storage media having computer-executable instructions embodied thereon that, when executed by a computer, causes the computer to perform operations. The operations include providing a falls risk assessment and a patient safety risk assessment within an electronic health record of a patient. The operations also include prompting a clinician at a clinician device to provide input to the falls risk assessment and the patient safety risk assessment for the patient. The operations further includes, based on the input, determining a safety assessment score for the patient. The operations also include providing the safety assessment score of the patient to the clinician via the clinician device. The operations further include prompting the clinician to initiate an order to place a camera in the room of the patient. The operations also include, based on the order, assigning a virtual sitter to the patient. The operations further include receiving an assignment of virtual guardrails for the patient. The virtual guardrails may include 3D zones positioned around a patient bed or chair, safety zones to detect tampering with invasive line or tube placement, safety zones for staff safety, patient elopement zones that provide a wide angle of a patient room to detect elopement, or visitor monitoring zones to prevent drug diversion and abuse.

Having briefly described embodiments of the present invention, an exemplary operating environment suitable for use in implementing embodiments of the present invention is described below. FIG. 1 provides an aspect of an example operating environment with which embodiments of the present invention may be implemented. The aspect of an operating environment is illustrated and designated generally as reference numeral 100.

Beginning with FIG. 1, an exemplary computing environment suitable for use in implementing embodiments of the present technology is shown. FIG. 1 is an exemplary computing environment (e.g., health-information computing-system environment) with which embodiments of the present technology may be implemented. The computing environment is illustrated and designated generally as reference numeral 100. The computing environment 100 is merely an example of one suitable computing environment and is not intended to suggest any limitation as to the scope of use or functionality of the present technology. Neither should the computing environment 100 be interpreted as having any dependency or requirement relating to any single component or combination of components illustrated therein. It will be appreciated by those having ordinary skill in the art that the connections illustrated in FIG. 1 are also exemplary as other methods, hardware, software, and devices for establishing a communications link between the components, devices, systems, and entities, as shown in FIG. 1, may be utilized in the implementation of the present technology. Although the connections are depicted using one or more solid lines, it will be understood by those having ordinary skill in the art that the exemplary connections of FIG. 1 may be hardwired or wireless, and may use intermediary components that have been omitted or not included in FIG. 1 for simplicity's sake. As such, the absence of components from FIG. 1 should not be interpreted as limiting the present technology to exclude additional components and combination(s) of components. Moreover, though devices and components are represented in FIG. 1 as singular devices and components, it will be appreciated that some embodiments may include a plurality of the devices and components such that FIG. 1 should not be considered as limiting the number of a device or component.

The present technology might be operational with numerous other special-purpose computing system environments or configurations. Examples of well-known computing systems, environments, and/or configurations that might be suitable for use with the present technology include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present technology may be operational and/or implemented across computing system environments such as a distributed or wireless "cloud" system. Cloud-based computing systems include a model of networked enterprise storage where data is stored in virtualized storage pools. The cloud-based networked enterprise storage may be public, private, or hosted by a third party, in embodiments. In some embodiments, computer programs or software (e.g., applications) are stored in the cloud and executed in the cloud. Generally, computing devices may access the cloud over a wireless network and any information stored in the cloud or computer programs run from the cloud. Accordingly, a cloud-based computing system may be distributed across multiple physical locations.

The present technology might be described in the context of computer-executable instructions, such as program modules, being executed by a computer. Exemplary program modules comprise routines, programs, objects, components, and data structures that perform particular tasks or implement particular abstract data types. The present technology might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including database 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Computer-readable media does not include signals per se.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations including operating systems, device drivers and the like. The remote computers might also be physically located in traditional and nontraditional clinical environments so that the entire medical community might be capable of integration on the network. The remote computers might be personal computers, servers, routers, network PCs, peer devices, other common network nodes, or the like and might comprise some or all of the elements described above in relation to the control server. The devices can be personal digital assistants or other like devices. Further, remote computers may be located in a variety of locations including in a medical or research environment, including clinical laboratories (e.g., molecular diagnostic laboratories), hospitals and other individual settings, ambulatory settings, medical billing and financial offices, hospital administration settings, home medical environments, and clinicians' offices. Medical providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; students; and the like. The remote computers 108 might also be physically located in nontraditional clinical environments so that the entire medical community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the database 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touchscreen, a pointing device (commonly referred to as a mouse), a trackball, or a touch pad. Other input devices comprise satellite dishes, scanners, or the like. Commands and information might also be sent directly from a remote medical device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
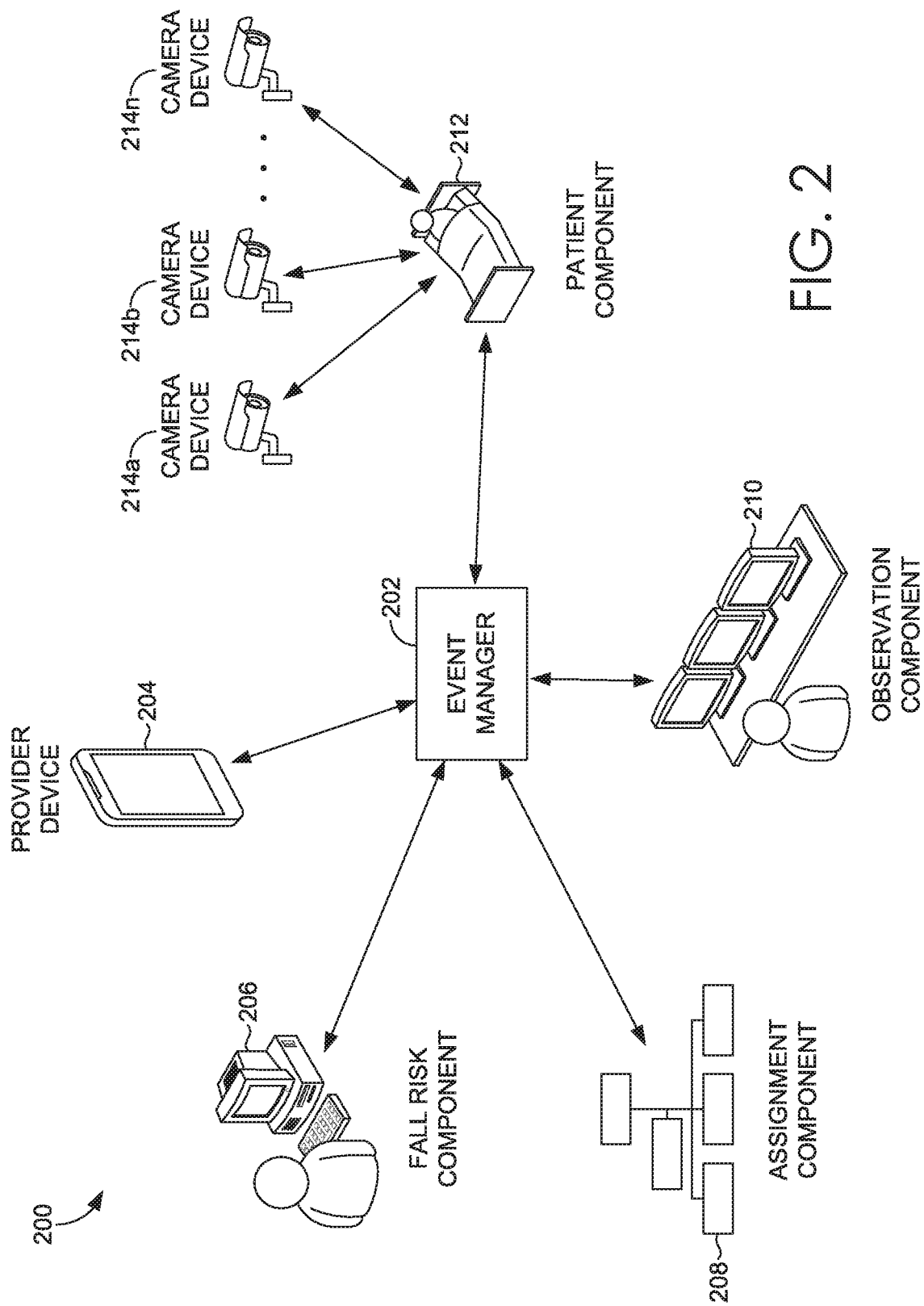
FIG. 2 depicts an exemplary framework of a virtual observation system suitable to implement embodiments of the present disclosure.

As shown in FIG. 2, an exemplary virtual observation system 200 comprises an event manager 202, a provider device 204, falls risk component 206, assignment component 208, observation component 210, patient component 212, and camera device(s) 214a-214n.

The exemplary virtual observation system 200 may be remotely located at a physical location with a data connection (e.g. USB, TCP/IP, etc.) to devices for observing a patient in real-time. The exemplary virtual observation system 200 may be on the same floor as the patient, on a different floor than the patient, in the same building as the patient, in a different building than the patient, or in a different facility than the patient. If the exemplary virtual observation system 200 is monitoring more than one patient, the patients may be located in different rooms, floors, buildings, or facilities from one another. The exemplary virtual observation system 200 may be in a single location or may be distributed amongst multiple locations.

Event manager 202 generally enables connectivity and communication between provider device 204, falls risk component 206, assignment component 208, observation component 210, patient component 212, and an EHR for the patient(s) being observed.

Provider device 204 generally receives alerts from the virtual observation system 200. The alerts may be provided to provider device(s) 204 of clinicians, a team of clinicians, or to a patient care technician (e.g., a physical sitter).

Falls risk component 206 generally enables a clinician to complete a falls risk assessment and patient safety risk assessment within the EHR of a patient. The clinician may be prompted to consider placing a camera at the bedside of the patient. Once the clinician determines the camera should be placed at the bedside of the patient, a notice is sent via the event manager 202 to observation component 210 and a provider device 204 (e.g., a technician trained to place the camera devices) that a camera needs to be placed.

Assignment component 208 generally assigns a patient to a particular clinician, team of clinicians, patient care technician, and/or virtual sitter so provider device(s) 204 corresponding to the assigned personnel can receive appropriate alerts, notifications, and patient requests, and can communicate with the patient and other assigned personnel. Assignment component 208 may be utilized to assign the location of a camera device(s) 214a-214n in the room of a patient or retrieve information corresponding to the assignment of a particular camera device(s) 214a-214n from the EHR of the patient.

Observation component 210 generally utilizes two-way camera technology to communicate with the patient via the patient component 212, communicate with a clinician or virtual sitter via provider device 204, and provides a command button panel that integrates with the EHR for documentation. A virtual sitter may be tasked to document at least once an hour. As described below, virtual guardrails can be customized for each patient. If a patient moves past the guardrail a visual cue is displayed by observation component 210 in a user interface. The virtual sitter may communicate to the patient via the camera device(s) 214a-214n and try to redirect the patient or select one of the buttons on the custom button panel (e.g., communicate an alert to and/or communicate with a clinician(s) directly).

Generally, patient component 212 streams data received from camera device(s) 214a-214n to the observation component 210 via the event manager 202. The patient component 212 may be integral to the camera device(s) 214a-214n or a distinctly separate apparatus from the camera device(s) 214a-214n possibly in a remote location from camera device(s) 214a-214n provided that the patient component 212 can receive data from the camera device(s) 214a-214n. The patient component 212 may be located in the monitored patient room, such as a hospital room or other clinical setting, bedroom, or living room. The patient component 212 may be connected to the observation component 210. The patient component and observation component 210 may be remotely located at any physical locations so long as a data connection exists (USB, TCP/IP or comparable) between the patient component 212, the observation component 210, and the camera device(s) 214a-214n.

The patient component 212 may receive data from a camera device(s) 214a-214n for a 3D zone (e.g., positioned around the patient bed or chair), a safety zone (i.e., to detect tampering with invasive line or tube placement or promote staff safety), a patient elopement zone (i.e., that provides a wide angle of a patient room to detect elopement), or a visitor monitoring zone (i.e., to prevent drug diversion and abuse). Patient component 212 may enable a virtual sitter or clinician to assign virtual guardrails to identify the boundaries of the 3D zone, the safety zone, the patient elopement zone, or the visitor monitoring zone. For example, the virtual guardrails may be assigned to a perimeter around the patient. It should be understood that the selection of a location of the virtual guardrails may vary with the individual. Virtual guardrails may be configured automatically by the patient component 212, may be configured automatically by the patient component 212 subject to confirmation and/or modification by a virtual sitter or clinician, or may be configured manually by a virtual sitter or clinician.

Camera device(s) 214a-214n generally communicates data, such as images of the patient room being monitored, to the patient component 212. The camera device(s) 214a-214n may enable two-way communication such that the patient can communicate with the virtual sitter and vice versa. Additionally, privacy mode and night vision may be provided by camera device(s) 214a-214n for patient safety. For example, in privacy mode, camera device(s) 214a-214n and/or patient component 212 may blur, pixelate, or otherwise obscure (e.g. automatically convert details of patients to cartoons, blocks, blobs, stick figures) images or videos. This may be done to protect patient privacy and modesty while still maintaining patient safety with the virtual sitter. Camera device(s) 214a-214n may be co-located with a patient room to be monitored. A patient room to be monitored may be monitored in a variety of environments, including, without limitation, a hospital, a home, a hospice care facility, a nursing home, an assisted living facility, an outpatient medical care facility, and the like.

The camera device(s) 214a-214n may be positioned where it is likely to capture images of the patient room to be monitored. For example, a camera device(s) 214a-214n may be oriented to take images of a bed, chair, or other location where a patient in the patient room to be monitored may spend a significant amount of time. In some embodiments, the camera device(s) 214a-214n may be oriented to take images of persons and/or objects entering and exiting the patient room to be monitored. In some embodiments, the camera device(s) 214a-214n may be oriented to take images of equipment (e.g., medical devices) that may be located in the patient room to be monitored.

Camera device(s) 214a-214n may capture data including 3D depth data, data defining one or more bounding boxes, skeletal object tracking data and/or blob or object tracking data. In some implementations, it may be desirable for the sensors to capture video only, or sound only, or video and sound. Alternatively, or additionally, if a virtual sitter is monitoring detailed images or video streams of patients, the data may be pixelated, or otherwise obscured (e.g. automatically convert details of patients to cartoons, blocks, blobs, stick figures). This may be done to protect patient privacy and modesty.

The camera device(s) 214a-214n may be permanently installed and activated upon an order initiated by the clinician, or may be temporarily set up in a room as needed. The patient in the patient room to be monitored may be under immediate medical care, e.g., in a medical facility under the supervision of a medical professional, or may not be under immediate care, e.g., in a clinical setting or other environment, possibly with a caregiver. A caregiver may be a medical professional or paraprofessional, such as an orderly, nurse's aide, nurse, or the like. A caregiver may also be a friend, relative, individual, company, or facility that provides assistance with daily living activities and/or medical care for individuals, such as individuals who are disabled, ill, injured, elderly, or otherwise in need of temporary or long-term assistance. In some instances, the person to be monitored may be self-sufficient and not under the immediate care of any other person or service provider.

Data associated with camera device(s) 114a-114n may be logged by observation component 210, in an EHR, or in a database. Data associated with camera device(s) 114a-114n may include, without limitation, a live image, video and/or audio feed; documentation received from a virtual sitter via the observation component 210; documentation received from a clinician via the fall risk component 206; communications provided to or received from the provider device 204 the individual(s) and/or groups to whom an alert was addressed; the response, if any, received or observed following an alert; and combinations thereof.

With reference to FIGS. 3-9, illustrative screen displays 300, 400, 500 . . . 900 of embodiments of the present invention are shown. It is understood that each of the illustrative screen displays are connected logically, such that they comprise a user interface designed for providing a virtual observation system. The screen displays may appear in any order and with any number of screen displays, without regard to whether the screen display is described or depicted herein. The screen displays may provide tools that enable utilizing a virtual observation system, in accordance with embodiments of the present invention.

Referring initially, to FIG. 3, an admission interface 300, in one embodiment, is initially provided. The admission interface 300 enables a clinician to select an assessment for the patient. For example, the clinician may select a falls risk assessment (e.g., admission skin/fall assessment or skin/fall assessment) or a patient safety risk assessment (e.g., patient observer safety score). This enables a clinician to provide input for a falls risk assessment and/or a patient safety risk assessment that can be utilized to determine the safety assessment score for the patient. The safety assessment score is utilized to prompt the clinician to initiate an order to place a camera in the room of the patient and assign a virtual sitter to the patient.

Figure 4:

Additionally, a clinician may select, via telemetry admission interface 300, a patient observer safety score assessment. As shown in FIG. 4, selecting the patient observer safety score assessment initiates a patient observer safety score interface 400 that enables the clinician to review documentation provided by the virtual sitter. The documentation may correspond to patient behavior, initiate communication with the clinician, and/or facilitate determining whether to continue or discontinue the virtual sitter for the patient.

Figure 5:
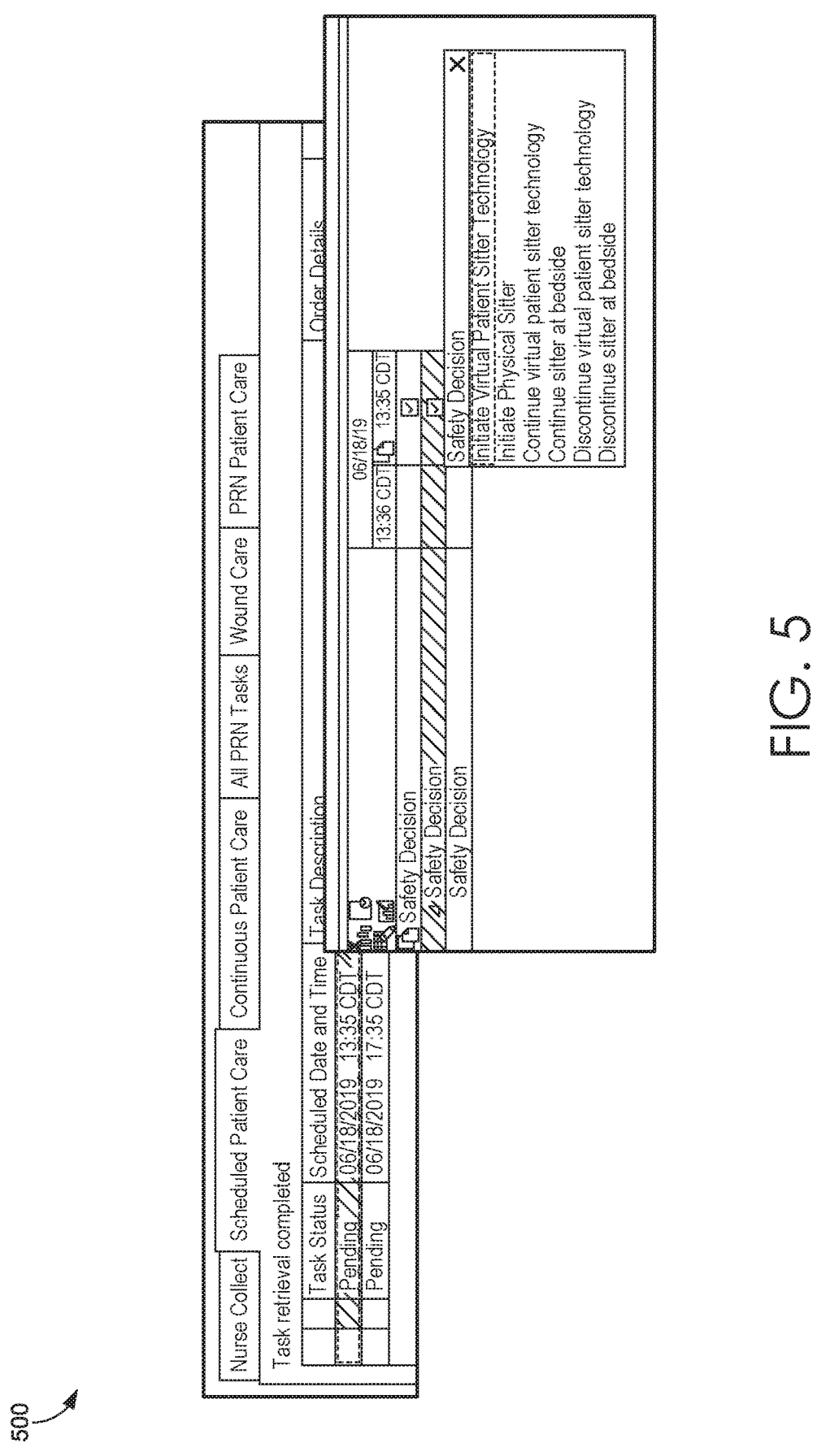

In FIG. 5, a safety decision interface 500 enables a clinician select the appropriate course of action for a patient. For example, if the safety assessment score meets a threshold, the clinician may select to initiate virtual patient sitter technology. If the safety assessment score meets a higher threshold, the clinician may select to initiate a physical sitter. Additionally, based on the documentation provided by the virtual sitter, the clinician may select to continue virtual patient sitter technology, continue sitter at bedside, discontinue virtual patient sitter technology, or discontinue sitter at bedside.

Figure 6:
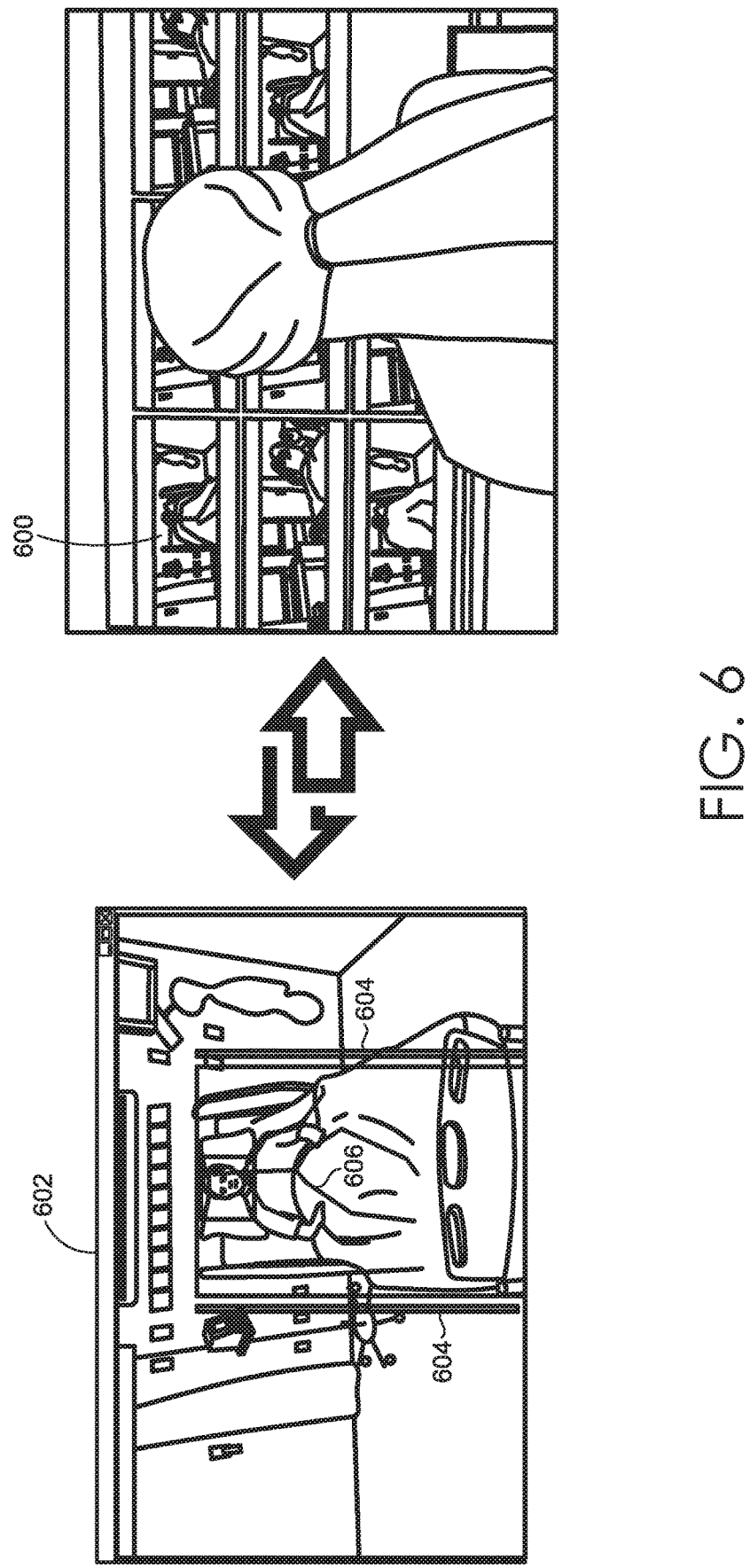

Turning now to FIG. 6, a monitoring station interface 600 enables the virtual sitter to observe up to twelve patients per monitoring station. Each patient room may have one or more camera devices to monitor the patients. A patient observation interface 602 enables the virtual sitter to focus on an individual patient. As shown in the patient observation interface 602, motion zones or virtual guardrails 604 illustrate the boundaries the patient must remain within. The patient may be tracked by the camera device(s) utilizing skeletal object tracking data (e.g., as depicted by skeleton 606). Importantly, the monitoring station interface 600 and patient observation interface 602 provide an additionally layer of care when a patient is alone in the room. Moreover, because a clinician does not need to be assigned as a physical sitter, more efficient capacity management and staffing level changes result.

Referring to FIG. 7, an observation interface 700 illustrates the workflow for a virtual sitter. The workflow may include various tasks. Upon selection of a particular task, a safety observation interface 702 enables the virtual sitter to document various patient activities, patient behaviors, interventions, or comments corresponding the patient. For example, patient activities may indicate the patient is in bed and awake, the patient is in bed and appears to have eyes closed, the patient is in a chair and awake, the patient is in a chair and appears to have eyes closed, the patient is ambulating in the room, the patient is in the bathroom, a provider is at bedside, the patient requests privacy for bedside care, visitors are at beside, or a fall has been observed.

As shown in FIG. 8, a control interface 800 enables the clinical or virtual sitter to perform various functions. For example, the control interface 800 includes buttons to document patient activities, such as the patient activities described above. Additionally, the control interface 800 includes buttons to provide warnings, request medication or food and drink for the patient, request staff assistance, or perform maintenance within the virtual observation system. Maintenance may include editing the patient or the placement or location of the virtual guardrails, turning on or off various features (e.g., night vision, video, audio), pixelating features of the video such as the face of the patient, rebooting the computing device in the patient room, restarting a camera device in the patient room, importing a camera device to or removing a camera device from the patient room, or resetting or swapping skeletons (representing the patient).

Figure 9:
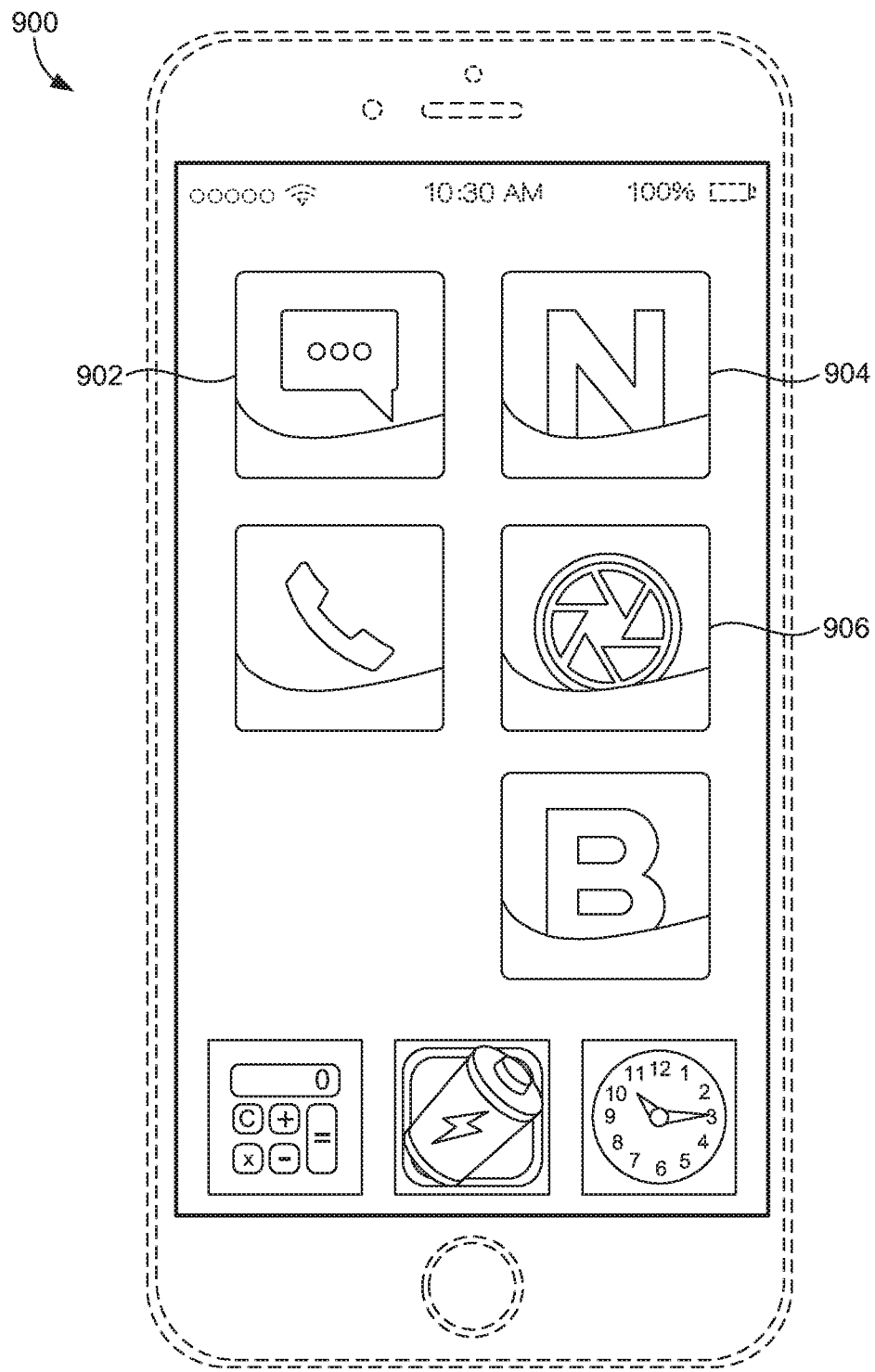

In FIG. 9, a mobile interface 900 illustrates various features that are provided to a clinician mobile device or a virtual sitter mobile device. A messenger button 902 provides a shared directory, secured text messaging, and clinical notifications and alerts (e.g., a patient is in sepsis, a patient observation is available, a medication has been prescribed). A nursing button 904 enables a clinician to review or document within an EHR for a patient (e.g., charts, orders or items, vitals, etc.), scan barcodes for administration of medications, order or review specimen collections. A camera device button 906 enables the clinician or virtual sitter to capture an image from a camera device and/or a chart for the patient.

Figure 10:
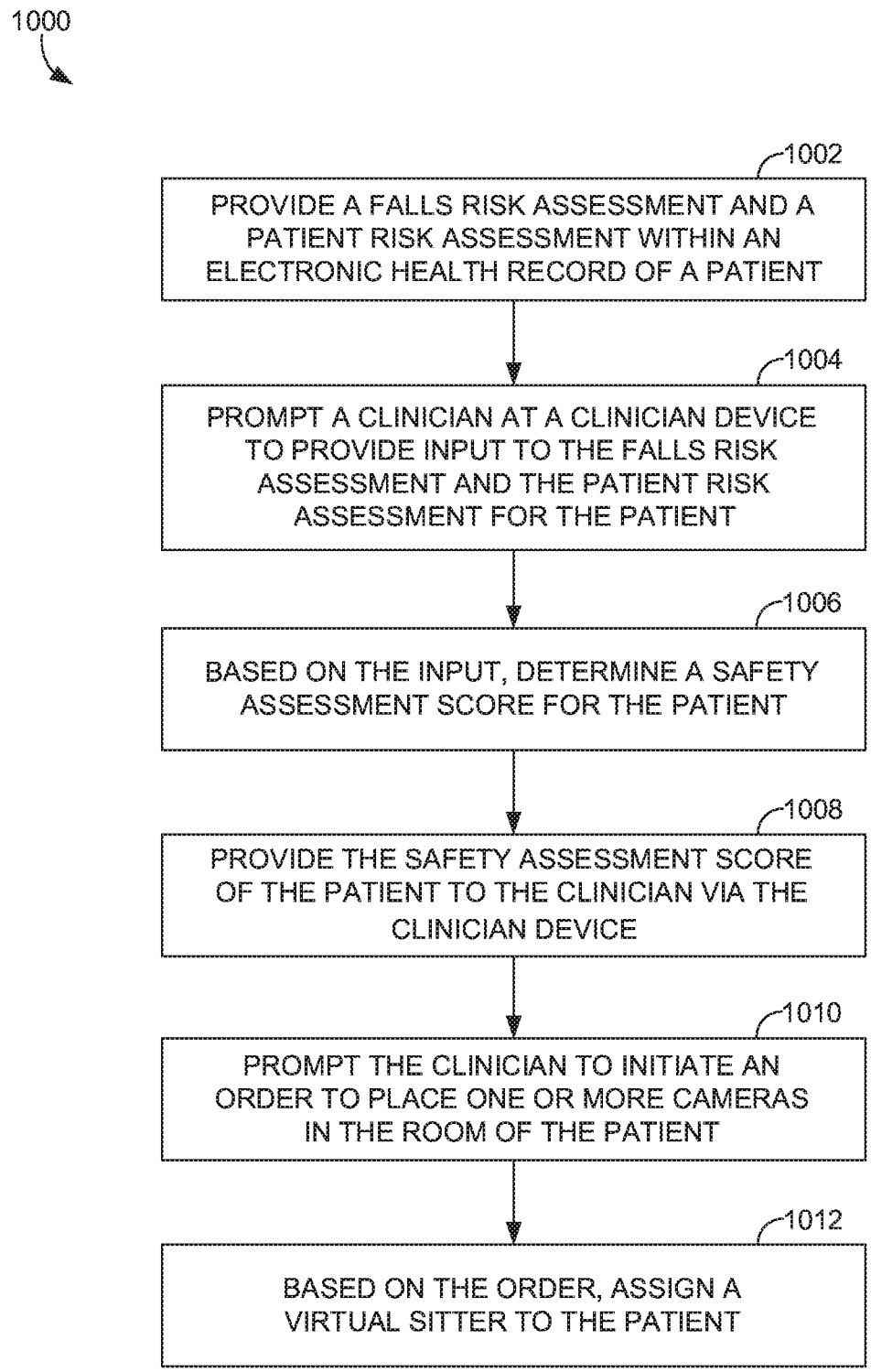
FIG. 10 is a flow diagram of a method for providing improved patient safety using virtual observation, in accordance with embodiments of the present invention.

Turning now to FIG. 10, a flow diagram is provided illustrating a method 1000 method for providing improved patient safety using virtual observation, in accordance with embodiments of the present invention. Method 1000 may be performed by any computing device (such as computing device described with respect to FIG. 1) with access to a virtual observation system (such as the one described with respect to FIG. 2) or by one or more components of the virtual observation system.

Initially, at step 1002, a falls risk assessment and a patient safety risk assessment are provided within an electronic health record of a patient. A clinician is prompted, at step 1004, to provide input via a clinician device to the falls risk assessment and the patient safety risk assessment for the patient. Based on the input, a safety assessment score is determined for the patient, at step 1006. The safety assessment score of the patient is provided, at step 1008, to the clinician via the clinician device. At step 1010, the clinician is prompted to initiate an order to place a camera in the room of the patient. Based on the order, a virtual sitter is assigned, at step 1012, to the patient.

In some embodiments, a virtual observation interface is provided. The virtual observation interface may enable the virtual sitter to communicate alerts and notifications corresponding to the patient to the clinician device, secure messages with the patient or the clinician, integrate with health care applications corresponding to the patient, and images and charts of the patient. The virtual sitter may be prompted to provide documentation at the virtual observation interface. For example, the clinician may schedule tasks at various intervals for the virtual sitter to document the patient's location within the room, behaviors of the patient, and the like. In some embodiments, the virtual observation interface enables the virtual observer to document patient activity, patient behavior, interventions, and interventions comments. Upon receiving documentation corresponding to patient activity or patient behavior, the virtual observation system may recommend or the clinician may determine whether to continue or discontinue the virtual sitter for the patient.

In some embodiments, virtual guardrails may be defined or assigned for the patient. For example, the virtual guardrails may be 3D zones positioned around a patient bed or chair. Additionally or alternatively, the virtual guardrails may be safety zones to detect tampering with invasive line or tube placement or to promote staff safety. In some embodiments, the virtual guardrails may be patient elopement zones that provide a wide angle of a patient room to detect elopement. The virtual guardrails may be visitor monitoring zones to prevent drug diversion and abuse.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A system having one or more processors configured to facilitate a plurality of operations, the operations comprising:
    determining based on a machine-learning electronic model whether to present a falls risk assessment (a) on a clinician device, (b) for clinical input comprising falls-risk assessment information (c) in order to include the falls-risk assessment information as an update in an electronic health record (EHR) of a patient, wherein:
        the machine-learning electronic model is trained by inputting, to the machine-learning electronic model, information corresponding to instances of medical information indicating patient assignment to a virtual sitter, and
        the determining comprises applying, to the trained machine-learning electronic model, an instance of medical information associated with the patient;
    after determining that the falls risk assessment is to be presented on the clinician device, causing presentation of a prompt at the clinician device for the clinical input comprising the falls-risk assessment information;
    based on the clinical input:
        (i) storing the falls-risk assessment information for the patient to the EHR; and
        (ii) initiating generation of an order to assign processor based virtual sitter technology,
        wherein the order is associated with activation of a processor coupled camera in a patient room, and wherein a processor based virtual sitter device is configured to electronically monitor electronic signal information associated with the camera from a location remote to the camera and electronically communicate an update associated with falls assessment information corresponding to the patient based on the monitoring;
    subsequent to assigning the virtual sitter technology, electronically receiving the update for the patient from the virtual sitter device, the update corresponding to the information and to data associated with operation of the camera after the assignment of the virtual sitter technology; and
    in response at least to receiving the update for the patient from the virtual sitter device:
        initiating an action via the one or more processors to discontinue the virtual sitter technology.

2. The system of claim 1, wherein the operations further comprise causing presentation of a prompt at a virtual observation interface of the virtual sitter device for entry of patient documentation via the virtual observation interface.

3. The system of claim 2, wherein the operations further comprise, in response to receiving documentation corresponding to patient behavior from the virtual sitter via the virtual observation interface, prompting a clinician at the clinician device to determine whether to continue or discontinue the virtual sitter for the patient.

4. The system of claim 1, wherein the operations further comprise receiving from the clinician device an assignment of virtual guardrails for the patient.

5. The system of claim 4, wherein the virtual guardrails comprise 3D zones positioned around a patient bed or chair.

6. The system of claim 4, wherein the virtual guardrails comprise safety zones configured to detect tampering with invasive line or tube placement.

7. The system of claim 4, wherein the virtual guardrails comprise patient elopement zones that provide a wide angle of a patient room and that are configured to detect elopement.

8. The system of claim 4, wherein the virtual guardrails comprise visitor monitoring zones configured to prevent drug diversion and abuse.

9. The system of claim 1, wherein the operations further comprise providing a virtual observation interface configured to enable a virtual observer to document patient activity, patient behavior, interventions, and interventions comments.

10. The system of claim 9, wherein the virtual observation interface is integrated with one or more health care applications corresponding to the patient and is further configured to enable the virtual sitter to communicate: alerts and notifications corresponding to the patient to the clinician device, secure messages with the patient or the clinician device, and images and charts of the patient.

11. A method, comprising:
    determining based on a machine-learning electronic model whether to present a falls risk assessment (a) on a clinician device, (b) for clinical input comprising falls-risk assessment information (c) in order to include the falls-risk assessment information as an update in an electronic health record (EHR) of a patient, wherein:
        the machine-learning electronic model is trained by inputting, to the machine-learning electronic model, information corresponding to instances of medical information indicating patient assignment to a virtual sitter, and
        the determining comprises applying, to the trained machine-learning electronic model, an instance of medical information associated with the patient;
    after determining that the falls risk assessment is to be presented on the clinician device, causing presentation of a prompt at the clinician device for the clinical input comprising the falls-risk assessment information;
    based on the clinical input:
        (i) storing the falls-risk assessment information for the patient to the EHR; and
        (ii) initiating generation of an order to assign processor based virtual sitter technology,
        wherein the order is associated with activation of a processor coupled camera in a patient room, and wherein a processor based virtual sitter device is configured to electronically monitor electronic signal information associated with the camera from a location remote to the camera and electronically communicate an update associated with falls assessment information corresponding to the patient based on the monitoring;

subsequent to assigning the virtual sitter technology, electronically receiving the update for the patient from the virtual sitter device, the update corresponding to the information and to data associated with operation of the camera after the assignment of the virtual sitter technology; and in response at least to receiving the update for the patient from the virtual sitter device:
  initiating via one or more processors an action to discontinue the virtual sitter technology.

12. The method of claim 11, further comprising receiving from the clinician device an assignment of virtual guardrails for the patient.

13. The method of claim 12, wherein the virtual guardrails comprise 3D zones positioned around a patient bed or chair.

14. The method of claim 12, wherein the virtual guardrails comprise safety zones that detect tampering with invasive line or tube placement.

15. The method of claim 12, wherein the virtual guardrails comprise patient elopement zones that provide a wide angle of a patient room and detect elopement.

16. The method of claim 12, wherein the virtual guardrails comprise visitor monitoring zones that prevent drug diversion and abuse.

17. One or more non-transitory media having instructions that, when executed by one or more processors, cause a plurality of operations, the operations comprising:
  determining based on a machine-learning electronic model whether to present a falls risk assessment (a) on a clinician device, (b) for clinical input comprising falls-risk assessment information (c) in order to include the falls-risk assessment information as an update in an electronic health record (EHR) of a patient, wherein:
    the machine-learning electronic model is trained by inputting, to the machine-learning electronic model, information corresponding to instances of medical information indicating patient assignment to a virtual sitter, and
    the determining comprises applying, to the trained machine-learning electronic model, an instance of medical information associated with the patient;
  after determining that the falls risk assessment is to be presented on the clinician device, causing presentation of a prompt at the clinician device for the clinical input comprising the falls-risk assessment information;
  based on the clinical input:
    (i) storing the falls-risk assessment information for the patient to the EHR; and
    (ii) initiating generation of an order to assign processor based virtual sitter technology,
    wherein the order is associated with activation of a processor coupled camera in a patient room, and wherein a processor based virtual sitter device is configured to electronically monitor electronic signal information associated with the camera from a location remote to the camera and electronically communicate an update associated with falls assessment information corresponding to the patient based on the monitoring;
  subsequent to assigning the virtual sitter technology, electronically receiving the update for the patient from the virtual sitter device, the update corresponding to the information and to data associated with operation of the camera after the assignment of the virtual sitter technology; and
  in response at least to receiving the update for the patient from the virtual sitter device:
    initiating via the one or more processors an action to discontinue the virtual sitter technology.

18. The one or more non-transitory media of claim 17, wherein the operations further comprise providing a virtual observation interface.

19. The one or more non-transitory media of claim 18, wherein the virtual observation interface is integrated with one or more health care applications corresponding to the patient and is configured: to enable a virtual observer to document patient activity, patient behavior, interventions, and interventions comments and to communicate: (i) alerts and notifications corresponding to the patient to the clinician device, (ii) secure messages with the patient or the clinician device, and (iii) images and charts of the patient.

20. The system of claim 1, wherein the machine-learning electronic model is trained using patient information corresponding to previous virtual sitter technology assignments.

21. The system of claim 1, wherein the operations further comprise causing presentation of a safety assessment score corresponding to the falls assessment information on the clinician device and determining whether the safety assessment score meets a threshold, and wherein the action is initiated in response to a determination that the safety assessment score meets the threshold.

22. The method of claim 11, further comprising determining whether to provide the falls risk assessment within the EHR based on applying the machine-learning electronic model to information associated with the EHR.

23. The method of claim 22, wherein determining to provide the falls risk assessment within the EHR indicates that the information associated with the EHR is determined to be similar to information associated with EHRs of other patients associated with a falls risk.

24. The method of claim 11, wherein initiating the order is based on applying the machine-learning electronic model to information associated with the EHR.

25. The method of claim 11, wherein generating the order indicates that information associated with the EHR is determined to be similar to information associated with EHRs of other virtual sitter technology recipients.

26. The method of claim 11, wherein the machine-learning electronic model is applied to information associated with the EHR.

27. The method of claim 11, wherein initiating the action to discontinue the virtual sitter technology is based on applying the machine-learning electronic model to information associated with the update.

28. The one or more non-transitory media of claim 17, wherein the operations further comprise determining to generate the order in response to an application of the machine-learning electronic model to information associated with the EHR.

29. The one or more non-transitory media of claim 17, wherein generating the order corresponds to information associated with the EHR being determined as similar to information associated with other assignments of virtual sitter technology.

30. The one or more non-transitory media of claim 17, wherein the initiation of the action to discontinue the virtual sitter technology indicates that information associated with the update is determined to be similar to information associated with EHRs of other virtual sitter technology discontinuance actions.

31. The one or more non-transitory media of claim 17, wherein initiating the action to discontinue the virtual sitter technology comprises applying the machine-learning electronic model to determine whether a second prompt should be presented on the clinician device for instructions on whether to continue or discontinue the virtual sitter technology for the patient.

32. The system of claim 4, wherein the operations further comprise: after the assignment of virtual guardrails for the patient, detecting tampering associated with one or both of an invasive line and a tube placement.

33. The method of claim 11, wherein the clinical input is entered at the clinician device responsive to content of the falls risk assessment and indicates a falls-risk of the patient, and wherein the training is based at least in part on a process selected from a group comprising supervised machine learning, reinforcement machine learning, and unsupervised machine learning.

34. The one or more non-transitory media of claim 17, wherein training the machine-learning electronic model is based at least in part on machine learning associated with the instances of medical information indicating patient assignment to a virtual sitter, and wherein the operations further comprise:

updating the machine-learning electronic model based on additional instances of medical information indicating patient assignment to a virtual sitter;

applying the updated machine-learning electronic model to a particular set of medical information; and determining, based on the applying of the updated machine-learning electronic model to the particular set of medical information, whether to present a particular falls risk assessment.

35. The one or more non-transitory media of claim 17, wherein the media stores one or more instructions that, when executed by the one or more processors, cause: retraining the machine-learning electronic model based on one or more model inputs associated with training data selected from a group comprising the clinical input, the falls-risk assessment information, the virtual sitter technology assignment, the information, and the update.

36. The one or more non-transitory media of claim 35, wherein the one or more instructions further cause applying, to the retrained machine-learning electronic model, an instance of medical information associated with another patient.

\* \* \* \* \*